(12) United States Patent
Agyin

(10) Patent No.: US 6,297,384 B1
(45) Date of Patent: Oct. 2, 2001

(54) PROCESS FOR THE PREPARATION OF 1,2,4-THIADIAZOLES

(75) Inventor: Joseph K. Agyin, San Antonio, TX (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/468,039

(22) Filed: Dec. 21, 1999

(51) Int. Cl.$^7$ ................................................. C07D 285/08

(52) U.S. Cl. ............................................................. 548/128

(58) Field of Search ............................................... 548/128

(56) References Cited

U.S. PATENT DOCUMENTS 5,376,670   12/1994   Conner et al. ........................ 514/383

OTHER PUBLICATIONS

Chemical Abstracts 123:339794, Khare et al.
Kurzer, Frederick, 1,2,4–Thiadiazolylureas. A Postcript to the Oxidative Cyclisation of Thionoamidines, J. Chem. Soc. Perkin Trans. 1 1985, pp 311–314.
Kurzer, F., Secker, J., Addition–Cyclisations of Ethoxycarbonyl Isothiocyanate with Hydrazine Derivatives as a Source of Thiadiazoles and Triazoles, Mar.–Apr. 1989, pp 355–360.
U.S. application No. 09/535,172 (7485R), filed Mar. 27, 2000.
U.S. application No. 09/535,173 (7486R) filed Mar. 27, 2000.

*Primary Examiner*—Robert Gerstl
(74) *Attorney, Agent, or Firm*—Rose ANN Dabek; Steven W. Miller

(57) ABSTRACT

3-[N'-(benzoyl)thioureido]-5-substituted-1,2,4-thiadiazoles are debenzoylated in an aqueous KOH solution. This process provides the 5-substituted-3-thioureido-1,2,4-thiadiazoles in unexpectedly high yield and purity as compared to similar processes employing NaOH.

22 Claims, No Drawings

PROCESS FOR THE PREPARATION OF 1,2,4-THIADIAZOLES

FIELD OF THE INVENTION

The present invention relates generally to processes for preparing 1,2,4-thiadiazoles, and more particularly to processes for preparing 5-phenyl-3-thioureido-1,2,4-thiadiazole.

BACKGROUND OF THE INVENTION 5-phenyl-3-thioureido-1,2,4-thiadiazole (PTT) is used in the preparation of agricultural fungicides. Kurzer (*J. Chem. Soc., Perkin Trans.* (1985), 1(2), 311–314) discloses the synthesis of PTT from 3-[N'-(benzoyl)thioureido]-5-phenyl-1,2,4-thiadiazole (BzPTT). The conversion is effected by treating the BzPTT with a boiling 3 M aqueous solution of NaOH for 6–8 minutes, followed by acidification of the reaction milieu with concentrated hydrochloric acid, and then basification with gaseous ammonia. The PTT is recrystallized in a solution of acetone/ethanol (1:1 v/v) (300 mL/g) or nitrobenzene (5 ml/g) to provide an overall 85% yield recovery, on a 10.2 g-scale reaction.

Kurzer (*J. Heterocycl. Chem.*, (1989), 26, 355) discloses the synthesis of 5-Phenyl-3-thioureido-1,2,4-thiadiazole (PTT) from 1-ethoxycarbonyl-3,5-(3'-phenyl-1',2',4'-thiadiazol-3'-yl) thiourea (EtPTT). EtPTT is converted to PTT by suspending the EtPTT in a boiling solution of ethanol and NaOH (3 M) with reflux for 1 hour, acidifying the reaction milieu with 3 M hydrochloric acid, and recrystallizing the PTT from dimethylformamide (DMF). The PTT was isolated in 72% yield, on a 1.54 g-scale reaction.

SUMMARY OF THE INVENTION

The present invention provides a method by which PTT is prepared by deprotecting BzPTT with an aqueous solution of KOH, preferably 2–3 M KOH. It has been discovered that the use of KOH provides PTT in both higher yields and purity than that achieved using NaOH.

It has been unexpectedly found that the process of the present invention generally does not require chromatographic purification of the PTT and provides PTT containing less than 10% by wt., preferably less than 5% by wt., more preferably less than 2% by wt., and most preferably less than 1% by wt. of undesired by-products.

In one aspect, the present invention provides a method for the preparation of a compound of the Formula I

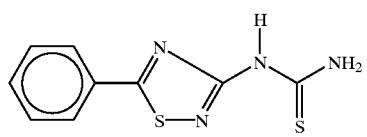

(I)

comprising the step of: (a) treating a compound of the Formula II

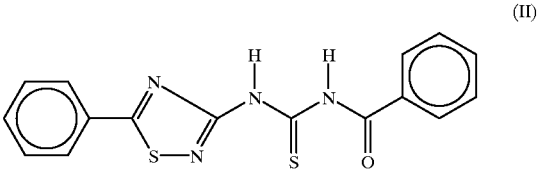

(II)

with KOH in the presence of a polar protic solvent, such as water or a combination of water and an organic solvent, at a temperature and for a time sufficient to form the compound of the Formula I.

Preferred embodiments of the method of the invention employ one or more of the following: (a) an aqueous solution as the polar protic solvent; (b) a reaction temperature of 50–60° C.; (c) rapid addition of a KOH-containing solution to the reaction solution; (d) a reaction time of 30–60 min.; (e) a 2–3 M KOH aqueous solution; and (f) vigorous agitation of the reaction milieu.

According to other preferred embodiments, the process can further comprise one or more of the following steps: (a) acidifying the reaction milieu with an inorganic acid; (b) basifying the acidic reaction milieu with an amine, such as ammonia, a primary amine, a secondary amine, a tertiary amine or a heterocyclic amine; (c) salting-out the compound of the Formula I from the reaction milieu; (d) isolating the compound of the Formula I by separating the solid form of the compound from a supernatant, such as the reaction solution; (e) drying the compound of the Formula I; (f) adjusting the pH of the reaction milieu to solubilize the benzoic acid by-product and leave the compound of the Formula I as a particulate solid in solution; (g) washing the compound of the Formula I with an aqueous solution; and (h) crystallizing the compound of the Formula I.

DETAILED DESCRIPTION OF THE INVENTION

Scheme I includes a comparison of the process of the prior art and that of the present invention. Although not shown in Scheme I, benzoic acid (BzOA) is a by-product of the reaction. The yields of the present process depend, among other things, upon the temperature at which the treatment is conducted and the equivalent ratio of the KOH to the compound of the Formula II.

The process of the present invention can be run at temperatures ranging from about 50° C. to a temperature which is at or below the boiling point of the organic solvent(s) used. The optimal temperature for running the reaction will depend, among other things, upon the organic solvent or combination of organic solvents used to run the reaction. If the reaction solution is water, the optimal temperature will generally range from about 50–70° C., preferably about 50–60° C., more preferably about 60° C. If the reaction solution comprises a combination of water and an organic solvent, the preferred reaction temperature is 60–65° C.

The process of the invention can be run at ambient to elevated pressure or generally from about atmospheric pressure or 1 atmosphere to about 10 atmospheres. The preferred pressure range is atmospheric pressure.

The process of the invention will be run for a period of time sufficient to form the compound of the Formula I in the desired yield and purity. The reaction time can take 0.5–1.5 hours, typically 0.5–1 hours, for completion and can vary according to the reaction temperature, the reaction solution employed, the equivalent ratio of KOH to the compound of the Formula II, the composition of the reaction solvent, the efficiency of the agitation employed during the reaction, and other reasons.

The concentration of a compound of the Formula II in the reaction solution can range from about 5–10%, preferably 5–6.5% by wt. based upon the final weight of the reaction mixture. Generally, about 9–11.5 volumes (L) of reaction solution per Kg of the compound of the Formula II are used.

The molar ratio of KOH:compound of the Formula II will vary between about 1:1 to about 10:1, preferably about 8:1 to about 10:1, and is most preferably about 9:1.

The compound of the Formula I can be isolated from the reaction mixture and purified according to the methods disclosed in Example 1 or according to other methods known to those of skill in the art. A first method of isolating the compound of the Formula I includes the steps of: (a) acidifying the reaction milieu with an inorganic acid; (b) basifying the resulting acidic milieu with an amine; (c) separating the particulate compound of the Formula I from the reaction supernatant; and (d) drying the compound of the Formula I. This first method is particularly useful when the reaction milieu contains no added buffering agents.

A second method of isolating the compound of the Formula I includes the steps of: (a) cooling the initial alkaline solution to 0° C.; (b) filtering the precipitated white product; (c) washing the solid with water and (d) drying. (See example 2.)

A third method of isolating the compound of the Formula I, preferably from a buffered reaction solution, includes the steps of: (a) acidifying the reaction milieu with an inorganic acid to a pH more than about 0.5 pH units greater than the pKa of benzoic acid; (b) separating the particulate compound of the Formula I from the reaction supernatant; and (c) drying the compound of the Formula I.

A fourth method of isolating the compound of the Formula I, preferably from an unbuffered reaction solution, includes the steps of: (a) acidifying the reaction milieu with an acidic buffered solution to a pH of about 0.5 pH units or greater than the pKa of benzoic acid; (b) separating the particulate compound of the Formula I from the reaction supernatant; and (c) drying the compound of the Formula I.

The solubility of the BzOA in the reaction solution is adjusted by controlling the pH and/or composition of the reaction solution. Generally, BzOA is completely soluble at concentrations below its saturation point in solutions having a pH about 1 pH unit greater than the pKa of BzOA. In its protonated form, BzOA can be solubilized in the reaction medium by increasing the concentration of organic solvent in the medium.

The method of the invention can be conducted in water, a biphasic reaction solution or a mixture of water and an organic solvent. A wide range of organic solvents can be employed in the presently claimed process. The organic solvent will generally be able to dissolve at least a portion of either one or both of the compound of the Formula I and the KOH. The solubility of the compounds of the Formulae I and/or II in the reaction solution may be very low. By proper design of the reaction solution, the solubility of these compounds may be adjusted to favor product formation or enhance product purity. For example, a reaction solvent which preferentially dissolves the compound of the Formula II over the compound of the Formula I will generally improve the yield and purity of the compound of the Formula I. The organic solvents that may be useful in the present invention include, but are not limited to, mixtures of water with water-miscible organic solvents.

Suitable polar solvents include dimethoxymethane, dimethoxyethane, tetrahydrofuran (THF), 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl ethyl ether, and t-butyl methyl ether.

Suitable protic solvents may include, by way of example and without limitation, water, ethylene glycol, diethylene glycol, diethylene glycol monomethyl ether, diethylene glycol monoethyl ether, glycerol, methanol, ethanol, 1-propanol and 2-propanol.

Suitable aprotic solvents may include, by way of example and without limitation, 1,3-dimethyl-3,4,5,6-tetrahydro-2 (1H)-pyrimidinone (DMPU), 1,3-dimethyl-2-imidazolidinone (DMI), N-methylpyrrolidinone (NMP), acetonitrile, dimethyl sulfoxide, propionitrile, ethyl methyl ketone, sulfolane, and tetramethylurea.

Suitable amines which can be used to basify the reaction milieu once it has been acidified include ammonia, ammonium hydroxide, primary amine, secondary amine, tertiary amine, aliphatic amine and aromatic amine. Exemplary amines include, but are not limited to, pyridine, aniline, benzylamine, n-butylamine, cyclohexylamine, diethylamine, diisopropylamine, dimethylamine, diphenylamine, ethylamine, ethylenediamine, hexamethylenediamine, morpholine, piperazine, piperidine, pyrrolidine, m-toluidine; trialkyl amines such as triethylamine, N,N-diisopropylethylamine, N,N-diethylcyclohexylamine, N,N-dimethylcyclohexylamine, N,N,N'-triethylenediamine, tetramethylethylenediamine (TMEDA); and substituted pyridines such as N,N-dimethylaminopyridine (DMAP), 4-pyrrolidinopyridine, 4-piperidinopyridine.

The acidic agent used to acidify the reaction milieu upon completion of the debenzoylation includes inorganic acids such as HCl, $H_2SO_4$, $H_2SO_3$, $H_3PO_4$, $H_3PO_3$, $HNO_3$, HF, HBr, HI, combinations thereof and acidic salts thereof; and organic acids such as trifluoroacetic acid (TFA), chloroacetic acid, alkyl sulfonic acids, ethanesulfonic acid, methanesulfonic acid, trifluoromethanesulfonic acid, formic acid, p-toluenesulfonic acid and combinations thereof.

Any known method of separating a solid from a liquid can be used in the present invention to separate the precipitated compound of the Formula I from a supernatant. Exemplary methods include filtration, centrifugation, decantation, settling of solids, and combinations thereof.

The compound of the Formula I can be dried using any known method of drying solids. If heat is employed during the drying process, it is preferred that the temperature of the compound of the Formula I not exceed its melting point. Exemplary methods of drying solids include air drying, oven drying, vacuum oven drying, tray drying, tumble drying, paddle drying freeze drying, heated drying, ambient temperature drying, and combinations thereof.

The compound of the Formula II was prepared according to Kurzer (*J Chem. Soc., Perkin Trans.* (1985), 1(2), 311–314), the disclosure of which is hereby incorporated by reference in its entirety. Unless otherwise noted, all other materials used herein are commercially available from sources such as Aldrich Chemical Co., Inc., Aceto Corporation, Acros Organics, Air Products, Apollo Scientific, Ltd., Albright & Wilson Americas, Bachem, AlliedSignal Corporation, BASF Aktiengesellschaft, Borregaard Fine Chemicals, Bridgewater Chemical, BNFL Fluorochemicals Ltd., Eastman Chemical Company, Elan Incorporated, Fluorochem Ltd., Fluka Chemie AG, Fisher Scientific, INDOFINE Chemical Company, Inc., JRD Fluorochemicals Ltd., Kanto Chemicals Co., Inc., Lancaster Synthesis Ltd., Research Organics Inc., Strem Chemicals, Inc., Wychem Ltd., or VWR Scientific.

The foregoing will be better understood with reference to the following examples which detail certain procedures for the manufacture of 1,2,4-thiadiazoles according to the present invention. All references made to these examples are for the purposes of illustration. They are not to be considered limiting as to the scope and nature of the present invention since further modifications of the disclosed invention will be apparent to those skilled in the art. All such modifications are deemed to be within the scope of the present invention.

EXAMPLE 1

Preparation of the 5-phenyl-3-thioureido-1,2,4-thiadiazole (PTT)

3-[N'-(benzoyl)thioureido]-5-phenyl-1,2,4-thiadiazole (BzPTT; 1 kg, 2.94 moles) was placed in a 12-L reaction vessel. A solution of KOH (8.8 L; 3.0 M in water) was added with stirring. The reaction milieu (initially yellow) was heated to 60° C. for about 1 hour or until completion with vigorous stirring. Completion of the reaction was determined either by a color change, e.g., from yellow (BzPTT) to white (PTT), or by monitoring by NMR. Concentrated HCl (2.2 L) was added with stirring at 0–10° C. to lower the pH to about 2–3 by Litmus paper. Concentrated ammonium hydroxide (241 mL) was added to the reaction milieu to raise the pH to about 8, which is more than 4 pH units greater than the pKa of the benzoic acid. After cooling in an ice bath for 30 minutes, the PTT was isolated by filtration in a Büchner funnel over filter paper and dried at room temperature overnight until dryness. The yield of PTT was about 97.4% and the product was about 99.7% pure as determined by HPLC. The $H^1$NMR and $^{13}C$ NMR spectrum of the product was consistent with that of a reference sample. Mp (253–255° C.) and mass spectroscopy were also used to identify the product.

EXAMPLE 2

To BzPTT (658 g, 1.93 moles) in a 12-L reaction vessel, equipped with a mechanical stirrer was added a 3M aqueous solution of KOH (560 g, 85.6% pure, 8.5 moles, in 5–7 L of $H_2O$). The reaction milieu was heated at 60° C. for 1 hour, with good stirring. The initial yellow color disappears, and the product precipitates out of the reaction mixture to form a white suspension. The reaction mixture is cooled down in an ice-bath to 0° C. and then filtered to collect the creamy-white product. After washing several times with water and then with ethanol/acetone (1:1,2 L) to afford 429.4 g (94%) of product.

EXAMPLE 3

A suspension of BzPTT (830 g, 2.44 moles) in 3M NaOH (878.4 g, 21.98 mol in 7.32 L of $H_2O$) was boiled for 15 minutes, cooled to 0° C., and treated with concentrated HCl (1.83 L) to give a thick, brownish precipitate, which is then basified by bubbling $NH_3(g)$ through the suspension. The resulting brownish white precipitate was filtered and washed with copious amounts of water and air-dried. The crude product was cleaned up by boiling in ethanol (ca. 8 L), cooling, and collecting the product by filtration. After recrystallization in DMF, 230 g (40% yield) of product was obtained as a light yellow solid. This was determined by HPLC to be 95% pure and contains trace amounts of DMF which could not be removed completely.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

I claim:

1. A process for the preparation of a compound of the Formula I

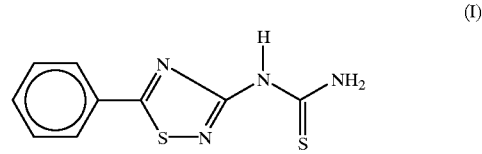

comprising the steps of:

(a) treating a compound of the Formula II

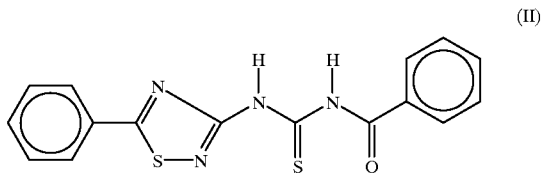

with KOH in the presence of a reaction solvent comprising an aqueous solvent at a temperature of about 50–70° C. and for a period of about 0.5–1.5 hours to form the compound of the formula I, wherein the concentration of KOH in the reaction solvent is about 2–3 M;

(b) separating the compound of the Formula I from the alkaline reaction solvent;

(c) washing the compound of the Formula I with an aqueous solution; and (d) drying the compound of the Formula I;

wherein the compound of Formula I contains less than 10% by wt. of undesired by-products.

2. A process for the preparation of a compound of the Formula I

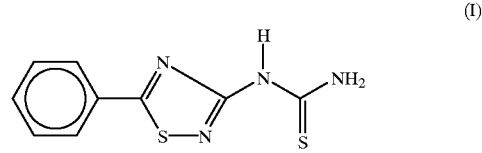

comprising the steps of: (a) treating a compound of the Formula II (II)

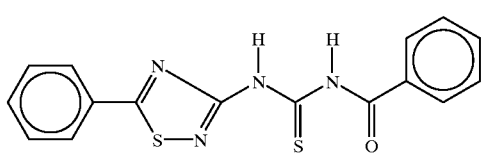

with KOH in the presence of a reaction solvent comprising an aqueous solvent at a temperature of about 50–70° C. and for a period of about 0.5–1.5 hours to form the compound of the formula I, wherein the concentration of KOH in the reaction solvent is about 2–3 M;

(b) acidifying the reaction solvent with an acid having a pKa less than that of benzoic acid after completion of the reaction;

(c) basifying the acidic reaction solvent to a pH greater than about 7;

(d) separating the compound of the Formula I from the alkaline reaction solvent;

(e) crystallizing the compound of the Formula I in a crystallization solvent; and (f) drying the compound of the Formula I;

wherein the compound of Formula I contains less than 10% by wt. of undesired by-products.

3. A process for the preparation of a compound of the Formula I (I)

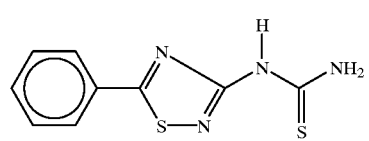

comprising the steps of: (a) treating a compound of the Formula II (II)

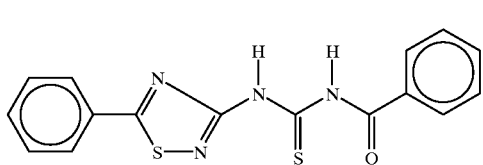

with KOH in the presence of a reaction solvent comprising a polar or protic solvent at a temperature of about 50–70° C. and for a period of about 0.5–1.5 hours to form the compound of the formula I; and (b) isolating the compound of Formula I by separating the solid form of the compound from the reaction solvent; wherein the compound of Formula I contains less than 5% by wt. of undesired by-products.

4. The process of claim 1 wherein the compound of Formula I contains less than 5% by wt. of undesired by-products.

5. The process of claim 2 wherein the compound of Formula I contains less than 5% by wt. of undesired by-products.

6. The process of claim 2 wherein in step (c) an amine is added to the acidic reaction solvent to basify the solvent.

7. The process of claim 6 wherein the amine is selected from the group consisting of ammonia, a primary amine, a secondary amine, a tertiary amine, a heterocyclic amine, and mixtures thereof.

8. The process of claim 6 wherein the amine is ammonium hydroxide.

9. The process of claim 3 wherein the KOH is added as a solution having a KOH concentration of about 2–3 M.

10. The process of claim 3 wherein the reaction solvent is selected from the group consisting of dimethoxymethane, dimethoxyethane, tetrahydrofuran (THF), 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl ethyl ether, t-butyl methyl ether, water, ethylene glycol, diethylene glycol, diethylene glycol monomethyl ether, diethylene glycol monoethyl ether, glycerol, methanol, ethanol, 1-propanol, 2-propanol, and combinations thereof.

11. The process of claim 3 further comprising at least one of the following steps:

(a) acidifying the reaction solvent with an inorganic acid after completion of the reaction;

(b) basifying the acidic reaction solvent with an amine;

(c) salting-out the compound of the Formula I from the reaction solvent;

(d) drying the compound of the Formula I;

(e) adjusting the pH of the reaction solvent to solubilize a benzoic acid by-product and leave the compound of the Formula I as a particulate solid in solution;

(f) washing the compound of the Formula I with an aqueous solution; and (g) crystallizing the compound of the Formula I.

12. The process of claim 11 wherein the amine in step (b) is selected from the group consisting of ammonia, a primary amine, a secondary amine, a tertiary amine, a heterocyclic amine, and mixtures thereof.

13. The process of claim 11 wherein the amine in step (b) is ammonium hydroxide.

14. The process of claim 3 further comprising the step of acidifying the reaction solvent with hydrochloric acid after completion of the reaction and before step (b).

15. The process of claim 14 further comprising the step of basifying the acidic reaction solvent with an amine before step (b).

16. The process of claim 15 wherein the amine is selected from the group consisting of ammonia, a primary amine, a secondary amine, a tertiary amine, a heterocyclic amine, and mixtures thereof.

17. The process of claim 15 wherein the amine is ammonium hydroxide.

18. The process of claim 3 further comprising the step of crystallizing the compound of the Formula I in a crystallization solvent.

19. The process of claim 18 further comprising the step of drying the compound of the Formula I.

20. The process of claim 13 wherein the molar ratio of KOH to compound of the Formula II is from about 1:1 to about 10:1.

21. The process of claim 3 further comprising the later step of washing the compound of the Formula I with an aqueous solution.

22. The process of claim 21 further comprising the later step of drying the compound of Formula I.

* * * * *

UNITED STATES PATENT AND TRADEMARK OFFICE
CERTIFICATE OF CORRECTION

PATENT NO.    : 6,297,384 B1
DATED         : October 2, 2001
INVENTOR(S)   : Joseph K. Agyin It is certified that error appears in the above-identified patent and that said Letters Patent is hereby corrected as shown below:

<u>Column 8,</u>
Line 58, delete "13" and insert therefor, -- 3 --.

Signed and Sealed this

Fourteenth Day of May, 2002

*Attest:*

JAMES E. ROGAN
*Attesting Officer*    *Director of the United States Patent and Trademark Office*